United States Patent
Jalenques (10) Patent No.: US 12,315,116 B2
(45) Date of Patent: May 27, 2025

(54) IMAGE PROCESSING PROCESS APPLIED TO COLONY COUNTERS IN MICROBIOLOGY

(71) Applicant: Interscience, St Nom la Breteche (FR)

(72) Inventor: Emmanuel Jalenques, St Nom la Breteche (FR)

(73) Assignee: INTERSCIENCE, St Nom la Breteche (FR)

( * ) Notice: Subject to any disclaimer, the term of this patent is extended or adjusted under 35 U.S.C. 154(b) by 0 days.

(21) Appl. No.: 18/407,425

(22) Filed: Jan. 8, 2024

(65) Prior Publication Data

US 2024/0185392 A1    Jun. 6, 2024

Related U.S. Application Data

(63) Continuation of application No. 17/223,784, filed on Apr. 6, 2021, now abandoned.

(30) Foreign Application Priority Data

Apr. 9, 2020 (FR) ..................................... 20 03596

(51) Int. Cl.
*G06T 5/50* (2006.01)
*G01N 15/14* (2024.01)
(Continued)

(52) U.S. Cl.
CPC ........... *G06T 5/50* (2013.01); *G01N 15/1433* (2024.01); *G06V 10/803* (2022.01); *G06V 20/69* (2022.01);
(Continued)

(58) Field of Classification Search
None
See application file for complete search history.

(56) References Cited

U.S. PATENT DOCUMENTS 3,920,311 A * 11/1975 Tsuda .................... G02F 1/1313
349/67
5,455,008 A    10/1995 Earley et al.
(Continued)

FOREIGN PATENT DOCUMENTS

EP          2807484 B1    5/2016
FR          3062133       7/2018
(Continued)

*Primary Examiner* — Michelle M Entezari Hausmann
(74) *Attorney, Agent, or Firm* — Thomas P. O'Connell; O'Connell Law Firm (57) ABSTRACT

A method and device for counting colonies in a sample in a medium. A bright field image is generated from light transmitted through the sample and the medium in a bright field configuration and collected by a detection unit, and a dark field image is generated from light scattered from the sample and the medium in a dark field configuration and collected by a detection unit. A fusion image is generated by a computer processing unit by combining two operand images, one an inverted image of the bright field image, and the other the dark field image. Colonies of the sample are counted by the computer processing unit based on processing of the fusion image. A single detection unit can generate the bright and dark field images, or the detection units can be separate. Light and dark diffusing surfaces can be separately retained or formed by a single diffuser.

12 Claims, 4 Drawing Sheets

(51) Int. Cl.
  *G01N 15/1433* (2024.01)
  *G06V 10/80* (2022.01)
  *G06V 20/69* (2022.01)

(52) U.S. Cl.
  CPC ... *G06V 20/698* (2022.01); *G01N 2015/1486* (2013.01); *G01N 2015/1497* (2013.01)

(56) References Cited

U.S. PATENT DOCUMENTS

| | | | |
|---|---|---|---|
| 6,288,780 B1 * | 9/2001 | Fairley | G01N 21/95623 |
| | | | 356/394 |
| 9,970,884 B1 * | 5/2018 | Nikitin | H04N 17/002 |
| 10,872,226 B2 | 12/2020 | Jalenques | |
| 11,022,553 B2 * | 6/2021 | Richard | G01N 21/8901 |
| 2003/0040104 A1 | 2/2003 | Barbera-Guillem | |
| 2003/0063274 A1 * | 4/2003 | Tsai | G01N 21/956 |
| | | | 356/237.5 |
| 2005/0123445 A1 | 6/2005 | Blecka et al. | |
| 2007/0258858 A1 | 11/2007 | Rasnow et al. | |
| 2012/0002034 A1 * | 1/2012 | Matsunobu | G06V 20/69 |
| | | | 348/79 |
| 2012/0258525 A1 | 10/2012 | Iizumi et al. | |
| 2013/0109051 A1 | 5/2013 | Li et al. | |
| 2015/0369752 A1 * | 12/2015 | Honda | G01N 21/9501 |
| | | | 356/237.2 |
| 2016/0320284 A1 * | 11/2016 | Spriggs | G01N 21/532 |
| 2017/0186173 A1 * | 6/2017 | Hakamada | G06T 7/97 |
| 2019/0064496 A1 * | 2/2019 | Vom | G02B 21/125 |
| 2019/0066284 A1 * | 2/2019 | Jiang | G06T 7/136 |
| 2019/0293566 A1 * | 9/2019 | Lu | G01N 21/8806 |
| 2020/0299748 A1 | 9/2020 | Jarvius | G01N 21/6428 |
| 2021/0231577 A1 * | 7/2021 | Pfister | G01N 21/9009 |
| 2021/0285056 A1 * | 9/2021 | Chukka | G06V 20/69 |
| 2021/0405044 A1 * | 12/2021 | Yang | G01N 33/68 |
| 2023/0273198 A1 * | 8/2023 | Ji | G01N 33/54326 |

FOREIGN PATENT DOCUMENTS

| | | |
|---|---|---|
| JP | H09187270 A | 7/1997 |
| JP | H11221070 A | 8/1999 |
| WO | WO9401528 | 1/1994 |

\* cited by examiner

IMAGE PROCESSING PROCESS APPLIED TO COLONY COUNTERS IN MICROBIOLOGY

RELATED APPLICATIONS

This application claims priority to French Application No. 2003596, filed Apr. 9, 2020 and to U.S. application Ser. No. 17/223,784, filed Apr. 6, 2021.

FIELD OF THE INVENTION

The present invention relates to the field of the detection of microorganisms in a growth medium. More particularly, the present invention relates to an image processing method applied to colony counters in microbiology, including in microbiological analysis and quality control. The imaging processing disclosed herein also finds application in the fields of the environment, the food industry, pharmacology, cosmetology, and research and development.

BACKGROUND OF THE INVENTION

Colony count is still commonly carried out by a manual counting of the colonies observed visually in a seeded culture medium. However, the prior art also discloses devices for counting colonies based on an acquisition of images of a sample comprising a previously inoculated culture medium and then a processing of the acquired images to determine a number of colonies.

For instance, European Patent No. EP2807484 to Advencis, which is incorporated herein by reference, describes a device for detecting microorganisms comprising a detection system comprising a scanner arranged to scan an area in which the upper surfaces of a set of inoculated samples are included with the samples positioned side by side on a surface of a platter. The images are then analyzed by image processing software so that colonies are identified and counted.

A drawback of such devices is that each of the samples to be analyzed is subjected to lighting throughout the time necessary for the image acquisition. Thus, when counting photosensitive microcolonies or when using photosensitive markers, it cannot be used. Another drawback of such devices is that, if it is not provided with an optical system allowing the focal length to be adjusted, the culture medium supports must be identical for all the samples. Where the device does have an optical system for adjusting the focal length, the time required to acquire all of the samples will be significantly increased.

French Patent No. FR3062133 and corresponding U.S. Pat. No. 10,872,226, both to the present inventor and both incorporated herein by reference, propose to resolve such drawbacks by teaching an apparatus and a method making it possible to reduce the time necessary for counting the final number of colonies present in a culture medium seeded with a sample as well as to reduce the levels of counting errors. However, preliminary settings, which are sometimes complicated, must be made on the device depending on the microcolonies.

Currently, several known light condition settings are used in colony counters, including the setting known as dark field imaging, for dark field microscopy. In dark field imaging, the illumination of the sample may be opposite the objective by transmission, on the same side by reflection, or even from the side. For example, dark field imagery may be obtained using light arranged grazing from below with a black background. This type of imaging is powerful because it illuminates very small particles, or diffuse elements, but reveals a lot of artifacts, such as textile fibers or dust.

Settings such as white field or bright field transmission imaging are also used. Such settings allow the detection of any obstacles absorbing light, letting a shadow stand out. Bright field transmission imaging is very robust because it does not create too much glare. However, it lacks sensitivity in some cases, such as when bacteria are too small or lack contrast.

Furthermore, with the colony counters previously mentioned, users must adjust certain parameters and create a setting where they fix the lighting and the type of algorithm for counting the colonies. These steps make the use of these machines complex.

SUMMARY OF THE INVENTION

In view of the foregoing, an object of embodiments of the invention is to simplify the use of colony counting machines, also referred to as colony counters. Another aim of embodiments of the invention is to improve the performance of colony counting, particularly with respect to environmental counts where any bacterial flora is sought and where it is necessary to count a wide variety of colonies on the same sample.

These and further objects, advantages, and details of the present invention will become obvious not only to one who reviews the present specification and drawings but also to those who have an opportunity to observe an embodiment of the image processing method and device disclosed herein in practice. Although the accomplishment of each of the foregoing objects in a single embodiment of the invention may be possible and indeed preferred, not all embodiments will seek or need to accomplish each and every potential advantage and function. Nonetheless, all such embodiments should be considered within the scope of the present invention.

In carrying forth certain objects of the invention, one practice of the method for counting colonies present in a sample placed in a support arranged to receive the sample and a solid nutrient medium comprises providing a computer processing unit, providing a detection unit in electronic communication with the computer processing unit, generating a bright field image, and generating a dark field image. The step of generating a bright field image can be performed from light transmitted through the sample and the medium in a bright field configuration to generate a bright field image with a light intensity having a maximum value (Ifcmax). The detection unit is positioned to collect the bright field image. The light intensity exhibits a value (Ifc (x, y)) less than the maximum value indicative of the presence of an occultation in the sample or the medium, and a threshold bright field light intensity (Ifcs) is considered to be indicative of a presence of a colony detected by the bright field image. The step of generating a dark field image can be performed based on light scattered from the sample and the medium in a dark field with the detection unit positioned to collect light scattered by the sample and the medium. In the presence of a colony or opacity deviation in the sample or the medium, the light scattered by the sample and the medium exhibits an increased value (Idf (x, y)) indicative of the presence of the colony or opacity deviation, and a threshold dark field light intensity (Idfs) is considered to be indicative of a presence of a colony detected by the dark field image. The method further comprises generating a fusion image (If) by operation of the computer processing unit with the fusion image (If) obtained by a linear combination of two operand images. One of the operand images is an inverted image of the bright field image, and the other operand image is the dark field image or one of the operand images is an inverted image of the dark field image and the other operand image is the bright field image. The computer processing unit is further operative to count colonies based on a processing of the fusion image (If) with the processing of the fusion image (If) comprising a thresholding of the fusion image based on a predetermined fusion image threshold light intensity (Ifs) above which a light intensity is considered not to be indicative of a presence of a colony and below which a light intensity is considered to be indicative of a presence of a colony. Depending on the processing parameters and formula employed, it would alternatively be within the scope of practices of the invention for the processing to comprise a thresholding of the fusion image based on a predetermined fusion image threshold light intensity (Ifs) below which a light intensity is considered not to be indicative of a presence of a colony and above which a light intensity is considered to be indicative of a presence of a colony.

In embodiments of the method, the computer processing unit is operative to generate an inverted dark field graph wherein the light intensity of pixels on the detection unit are graphed in x and y directions as Idf (x,y) and wherein the inverted dark field graph is obtained by the formula Idfinv (x, y)=Idfmax−Idf (x, y). It is further disclosed herein for the fusion image (If) obtained by the linear combination of the two operand images to be established by the computer processing unit by addition based on the formula If (x, y)=Idfinv (x, y)+Ifc (x, y).

In particular practices of the invention, the fusion image (If) obtained by the linear combination of the two operand images is operative to produce an indication of a presence of a colony with the fusion image threshold light intensity (Ifs) and the computer processing unit operative to indicate a presence of a colony including in instances wherein the threshold bright field light intensity (Ifcs) would not be met to be indicative of a presence of a colony detected by the bright field image and including in instances wherein the threshold dark field light intensity (Idfs) would not be met to be indicative of a presence of a colony detected by the dark field image. With that, the processing method and device can provide an indication of the presence and location of a colony that would not be found by dark field or light field imaging taken alone.

Embodiments of the invention can alternatively be characterized as an image processing device for counting colonies present in a sample. The device is provided with a location adapted to receive a support arranged to receive a solid nutrient medium and the sample. The image processing device includes a detection unit operative to generate a bright field image from light transmitted through the sample and the medium in a bright field configuration and collected by the detection unit. The bright field image has a light intensity with a maximum value (Ifcmax), and the detection unit is positioned to collect the bright field image. The light intensity exhibits a value (Ifc (x, y)) less than the maximum value indicative of the presence of an occultation in the sample or the medium, and a threshold bright field light intensity (Ifcs) may be considered to be indicative of a presence of a colony detected by the bright field image. The detection unit is further operative to generate a dark field image from light scattered from the sample and the medium in a dark field configuration and collected by the detection unit with the detection unit positioned to collect light scattered by the sample and the medium. In the presence of a colony or opacity deviation in the sample or the medium, the light scattered by the sample and the medium exhibits an increased value (Idf (x, y)) indicative of the presence of the colony or opacity deviation, and a threshold dark field light intensity (Idfs) can be considered indicative of a presence of a colony detected by the dark field image. A computer processing unit is operative to generate a fusion image (If) with the fusion image (If) obtained by a linear combination of two operand images. One of the operand images is an inverted image of the bright field image, and the other operand image is the dark field image. Alternatively, one of the operand images is an inverted image of the dark field image while the other operand image is the bright field image. The computer processing unit is operative to count colonies of the sample based on a processing of the fusion image (If) with the processing of the fusion image (If) comprising a thresholding of the fusion image based on a predetermined fusion image threshold light intensity (Ifs) above which a light intensity is considered not to be indicative of a presence of a colony and below which a light intensity is considered to be indicative of a presence of a colony. Again, it would alternatively be within the scope of the invention for the processing to comprise a thresholding of the fusion image based on a predetermined fusion image threshold light intensity (Ifs) below which a light intensity is considered not to be indicative of a presence of a colony and above which a light intensity is considered to be indicative of a presence of a colony.

Alternatively characterized, a practice of the method for counting colonies present in a sample placed in a support arranged to receive the sample and a solid nutrient medium comprises generating a bright field image from light transmitted through the sample and the medium in a bright field configuration and collected by a detection unit; generating a dark field image from light scattered from the sample and the medium in a dark field configuration and collected by a detection unit; generating a fusion image by a computer processing unit, the fusion image obtained by combining two operand images, one of the operand images being an inverted image of the bright field image, respectively in dark field, and the other operand image being the dark field image, respectively in bright field; and counting colonies of the sample by the computer processing unit based on a processing of the fusion image. Stated alternatively, one of the operand images is an inverted image of the bright field image while the other operand image is the dark field image or one of the operand images is an inverted image of the dark field image and the other operand image is the bright field image.

The step of generating the fusion image can again be carried out by the linear combination of the two operand images. For instance, the combination of the two operand images could be performed by addition. It is further disclosed herein that the processing of the fusion image can be carried out by a thresholding of the fusion image with reliance on a predetermined threshold.

Embodiments of the image processing device for counting colonies present in a sample are further disclosed wherein a detection unit is arranged to generate a bright field image from light transmitted through the sample and the medium in a bright field configuration and collected by the detection unit, and a detection unit, which may be the same or a different detection unit, is arranged to generate a dark field image from light scattered from the sample and the medium in a dark field configuration and collected by the detection unit. Thus, within the scope of the invention, the detection units can comprise separate detection units or can be formed as a single detection unit. A computer processing unit is arranged to generate a fusion image that is obtained by combining two operand images. One of the operand images is an inverted image of the bright field image, respectively in dark field. The other operand image is a dark field image, respectively in a bright field. The concept may again be alternatively stated as one of the operand images being an inverted image of the bright field image while the other operand image is the dark field image or one of the operand images being an inverted image of the dark field image and the other operand image is the bright field image. The computer processing unit is configured to count a number of colonies of the sample based on a processing of the fusion image.

Embodiments of the image processing device can further include a light diffusing surface and a bright field light source for establishing the bright field configuration and a dark diffusing surface and a dark field light source for establishing the dark field configuration. In certain practices of the invention, the bright field light source comprises a first plurality of light emitting diodes, and the dark field light source comprises a second plurality of light emitting diodes.

As disclosed herein, the computer processing unit is selectively operative to establish the bright field configuration wherein the dark field light source is extinguished and the bright field light source is illuminated to illuminate the medium and the sample with light diffused by the light diffusing surface. The computer processing unit is further selectively operative to establish the dark field configuration wherein the bright field light source is extinguished and the dark field light source is illuminated to illuminate the medium and the sample with light diffused by the dark diffusing surface.

Within the scope of the invention, the light diffusing surface and the dark diffusing surface can be separate. Alternatively, the light diffusing surface and the dark diffusing surface can be formed by a single diffuser.

Thus, according to a first aspect of the invention, a method is provided for counting colonies present in a sample placed in a support arranged to receive the sample and a solid nutrient medium. The method comprises generating a bright field image, by a first detection member or unit, from light transmitted from the support in a bright field configuration and collected by a first collection member; generating a dark field image, by a second detection member or unit, from light scattered from the medium in a dark field configuration and collected by the first collection member; generating what may be referred to as a fusion image, by a processing unit, obtained by combining two operand images, one of the operand images being an inverted image of the image in bright field, respectively in dark field, and the other operand image being the image in dark field, respectively in bright field; and counting the colonies, by the processing unit, from a processing of the fusion image.

The first detection member and the second detection member may be identical or different. A detection member can, by way of non-limiting example, be a matrix photoelectric sensor.

The processing unit configured to generate the fusion image and the processing unit configured to count colonies can be the same or separate. The processing unit can, for example, be a computing unit equipped with electronic storage and processing.

Advantageously, the generation of the fusion image can be obtained by linear combination of the two operand images, preferably by addition. Of course, several operand images could be implemented, each of the operand images possibly being of the bright field or dark field type. Other lighting can be used, such as but not limited to overhead lighting that performs well in opaque growing media. The processing of the fusion image may include thresholding of the fusion image from a predetermined threshold.

Alternatively, image processing can be performed by a neural network trained to count a number of colonies from a fusion image.

According to a second aspect of the invention, a device is provided for counting colonies present in a sample, the device provided with a location designed to receive a support arranged to receive a solid nutrient medium and the sample. The device comprises a first detection unit, alternatively referred to as a first detection member or a first collection unit, arranged to generate a bright field image, from a light transmitted from the location, that is to say by the sample when it is present in the support, in a clear field configuration and collected by the first collection unit; a second detection unit, alternatively referred to as a second detection member or second collection unit, arranged to generate a dark field image, from light scattered from the location, that is to say by the sample when it is present in the support, in a dark field configuration and collected by the second collection unit; a processing unit arranged to generate a fusion image, the fusion image obtained by combining two operand images, one of the operand images being an inverted image of the image in bright field, respectively in dark field, and the other operand image being the image in dark field, respectively in bright field; and a processing unit for counting colonies by a processing of the fusion image.

In embodiments of the invention, the first and the second detection members can be formed by a single detection member, and the processing unit can be arranged to selectively control, in a bright field configuration, the replacement of a dark diffusing surface by a light diffusing surface, turning off light emitting diodes for a dark field configuration, turning on light emitting diodes for a bright field configuration and, in a dark field configuration, replacing the light diffusing surface with the dark diffusing surface, switching off the light emitting diodes for a bright field configuration and switching on the light emitting diodes for a dark field configuration.

According to one possibility, the first and second detection members can be formed by a single detection member. Alternatively, the first and second detection members can be separate. The device can further comprise a diffuser device forming both a light surface for bright field configuration and a dark surface for the dark field configuration. Alternatively, separate diffusers can be employed.

One will appreciate that the foregoing discussion broadly outlines the more important goals and features of the invention to enable a better understanding of the detailed description that follows and to instill a better appreciation of the inventor's contribution to the art. Before any particular embodiment or aspect thereof is explained in detail, it must be made clear that the following details of construction and illustrations of inventive concepts are mere examples of the many possible manifestations of the invention.

BRIEF DESCRIPTION OF THE DRAWINGS

Other characteristics and advantages of the invention will become apparent on reading the detailed description that follows with further reference to the accompanying drawings wherein like numbers are used to indicate like components and wherein.

DETAILED DESCRIPTION OF PREFERRED EMBODIMENTS

The present invention for an imaging processing method and device for counting colonies in a sample is subject to a wide variety of embodiments within the scope of the invention. However, to ensure that one skilled in the art will be able to understand and, in appropriate cases, practice the present invention, certain preferred embodiments of the image processing process and device are described below with reference to the accompanying drawing figures.

Methods and devices incorporating only one characteristic or a selection of characteristics described herein, potentially isolated from other characteristics, shall nonetheless be within the scope of the invention except as the claims may expressly exclude. This is particularly the case where the selected characteristics confer a technical advantage or otherwise differentiate from the prior art.

Figure 1:
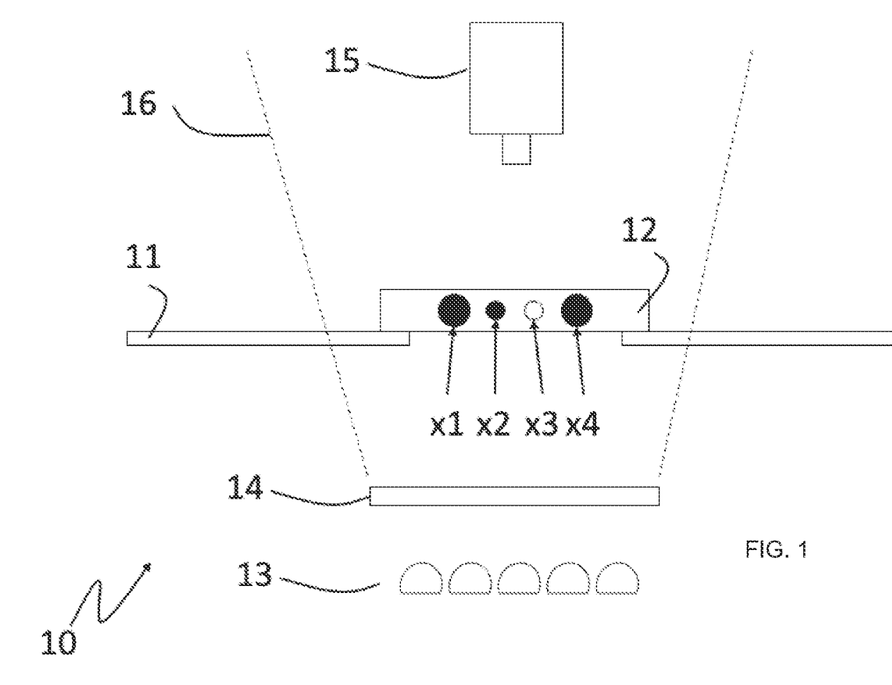
FIG. 1 is a side view of a bright field imaging setup according to the invention.

A method and device for counting colonies present in a sample is now described. Referring first to FIG. 1, a bright field imaging device is schematically depicted and indicated generally at 10. The imaging device 10 is provided with a support 11 that is arranged to receive and support a sample to be analyzed. Here, the sample comprises a sample retained by a Petri dish, which is indicated at 12. Several elements corresponding to positions x1, x2, x3, x4 are referenced to schematically represent the reality of the contents of the Petri dish 12.

The imaging device 10 is further equipped with a plurality of light sources 13, which here comprise a plurality of light emitting diodes 13. The imaging device 10 further includes a diffuser 14 with a white surface and a matrix photoelectric sensor 15. The plurality of light emitting diodes 13 and the diffuser 14 are disposed on the side opposite the matrix photoelectric sensor 15 with respect to the Petri dish 12.

The different components are arranged so that the matrix photoelectric sensor 15 and the Petri dish 12 are in a cone 16 of light diffused by the diffuser 14. The cone 16 is shown schematically in the figure by dotted lines. When the light emitting diodes 13 are in an on condition and in the absence of a colony in the Petri dish, the image formed by the photoelectric matrix sensor 15 is a white background image.

The light intensity of a pixel considered to be arranged in relation to x and y axes on the detection surface of the matrix photoelectric sensor 15 can be denoted Ifc (x, y).

The matrix photoelectric sensor 15 may be referred to as a first collection member or unit. The matrix photoelectric sensor 15 is arranged to collect light transmitted by the sample in the Petri dish 12 in a bright field configuration to generate a bright field image.

Figure 2:
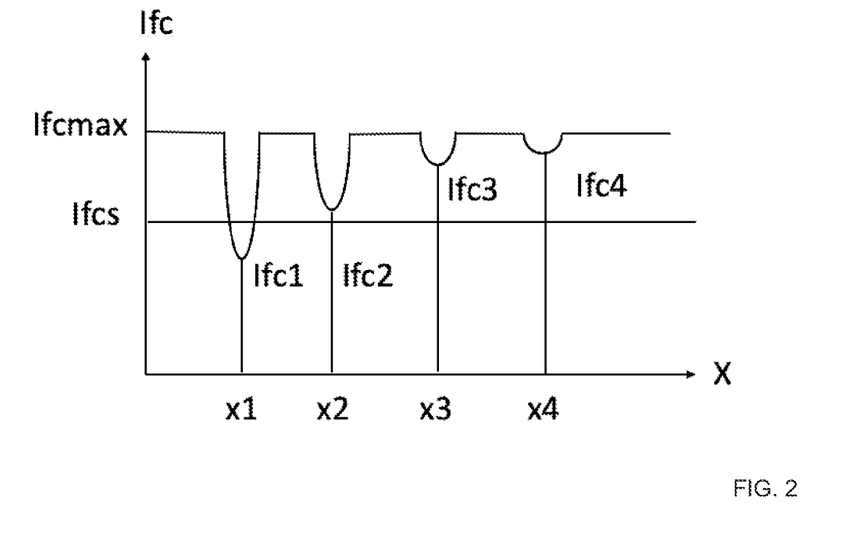
FIG. 2 is a graphical representation of the pixel brightness levels in the bright field imaging setup of FIG. 1.

FIG. 2 provides a graph of pixel light intensity Ifc along a column or row of the detection surface of the matrix photoelectric sensor 15 along an optical axis. The light intensity I is represented on the ordinate while the different pixels of the column or row are represented on the abscissa X.

In the absence of a colony, the light intensity Ifc has a maximum value denoted Icmax. The maximum value can be approximately equal to 255. Occasionally, the light intensity Ifc exhibits other values, denoted Ifc1, Ifc2, Ifc3 and Ifc4, possibly different but less than Ifcmax. In the graph, the light intensities Ifc can be perceived to be in the following relation of order: Ifc1<Ifc2<Ifc3<Ifc4.

The value Ifc1 marks the presence of an occultation of the light directly received by the matrix photoelectric sensor 15. Here, Ifc1<Ifcmax. We can thus assume that a colony is present at position x1 corresponding to the value Ifc1. However, since the Ifc3 and Ifc4 values are close to Ifcmax, it can be assumed that there is no colony at positions x3 and x4.

The value Ifc2 being intermediate between Ifc1 and that of Ifc3, respectively Ifc4, there may be a doubt about the presence of a colony at position x2 corresponding to Ifc2. Indeed, the x2 position may, for example, correspond to an opacity defect in the Petri dish, and not to the presence of a colony.

The decision as to the presence of a colony could be made by thresholding, specifically by determining a threshold Ifcs<Ifcmax above which an intensity Ifc is considered not to be indicative of the presence of a colony and below which an intensity Ifc is considered to be indicative of the presence of a colony. In the graph of FIG. 2, the following order can be perceived: Ifc1<Ifcs<Ifc2<Ifc3<Ifc4. Based on the threshold Ifcs, the following decision could be made: that there is a presence of a colony at x1 and an absence of colonies at x2, x3, and x4.

Figure 3:
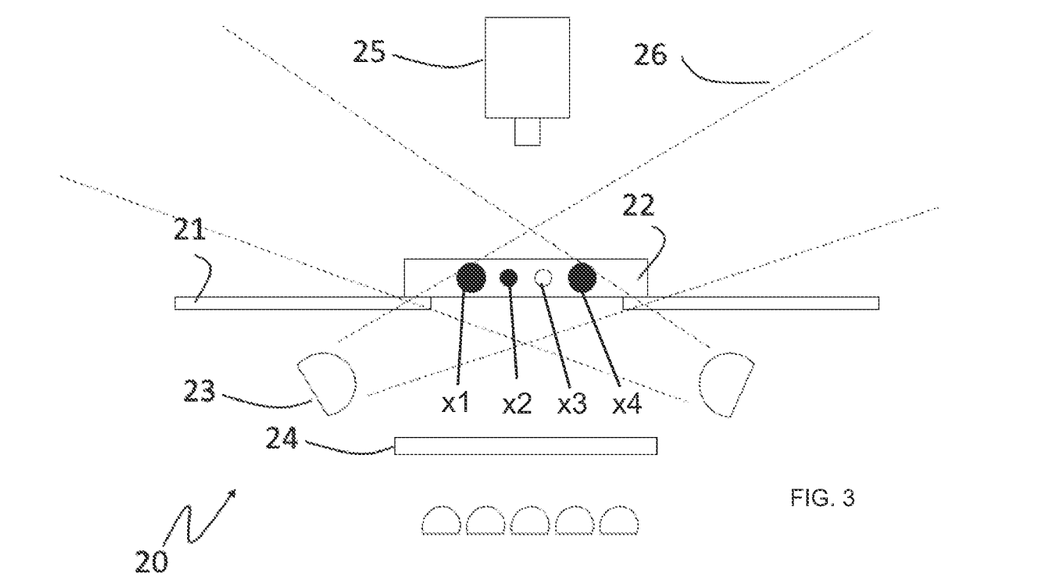
FIG. 3 is a side view of a dark field imaging setup according to the invention.

Referring to FIG. 3, a dark field imaging device 20 is schematically shown. The imaging device 20 is provided with a support 21 that is arranged to receive a Petri dish 22 that retains a nutrient medium and a seeded sample to be analyzed. More particularly with reference to the Petri dish 22, several elements corresponding to positions x1, x2, x3, x4 are referenced to schematically represent the reality of the contents of the Petri dish 22. As further explained herein, the x1 and x4 positions represented by black disks indicate the presence of large colonies. The x2 position indicates the presence of a more moderate colony, and the x3 position represents an artifact.

The imaging device 20 is further equipped with a plurality of light sources comprising light-emitting diodes 23. The device 20 further incorporates a diffuser 24 with a black surface and a matrix photoelectric sensor 25 that is provided with an optical axis. The plurality of light emitting diodes 23 and the diffuser 24 are both disposed on the side opposite the matrix photoelectric sensor with respect to the Petri dish 22.

Each of the light-emitting diodes 23 has an axis of light emission forming an angle greater than 60° with respect to the optical axis of the collector 25. The components of the device 20 are arranged so that the matrix photoelectric sensor 25 is not in the light cone 26 established by the light-emitting diodes 23 while the Petri dish 22 is in the light cone 26 diffused by the diffuser 24. The cone 26 is shown schematically in the figure by dotted lines. When the light-emitting diodes 23 are on, in the absence of a colony in the Petri dish 22, the image formed by the matrix photoelectric sensor 25 is a black-field image, since no light ray directly reaches the sensor 25.

The light intensity of a pixel arranged in x and y on the detection surface of the matrix photoelectric sensor 25 can be denoted Idf (x, y).

The matrix photoelectric sensor 25 can thus be considered a second collection member. The matrix photoelectric sensor 25 is arranged to collect light scattered by the sample of the Petri dish 22 in a dark field configuration to generate a dark field image.

Figure 4:
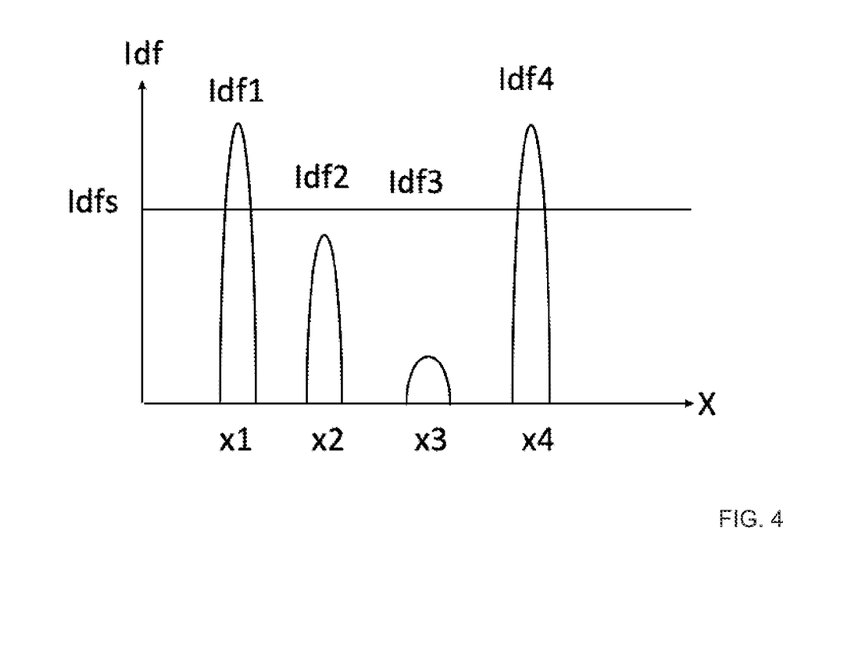
FIG. 4 is a graphical representation of the pixel brightness levels in the dark field imaging setup of FIG. 3.

FIG. 4 illustrates an intensity level of the pixels according to a column or a row on the detection surface of the matrix photoelectric sensor 25. The light intensity Idf is represented on the ordinate while the different pixels of the column or row are represented on the abscissa.

The graph depicts the light intensities Idf to be in the following relation of order: $Idf1=Idf4>Idf2>Idf3$. The Idf1 and Idf4 values indicate the presence of light scattering directly and its reception by the photoelectric matrix sensor 25. Since the Idf3 value is close to 0, it can be assumed that there is no colony at position x3.

Since the Idf2 value is intermediate between Idf1 and 0, there may be doubt about the presence of a colony at position x2 corresponding to Idf2. Indeed, the x2 position may, for example, correspond to an opacity defect in the Petri dish 22, and not to the presence of a colony.

The decision could be taken by thresholding wherein a threshold Idfs is determined above which an intensity Idf is considered indicative of the presence of a colony and below which an intensity Idf is considered indicative of the absence of a colony.

One will again note on the graph the following relation of order: $Idf1=Idf4>Idfs>Idf2>Idf3$. In this case, the following decision would be made: presence of a colony at x1 and x4 and absence of colonies at x2 and x3.

It is further noted that, depending on the technique used, the conclusions will not be the same: in a bright field imaging setting, the presence of a colony at x1 is detected and the absence of colonies at x2, x3 and x4 is detected whereas in a dark field imaging setting, the presence of a colony at x1 and x4 is detected and the absence of colonies at x2 and x3 is detected.

Figure 5:
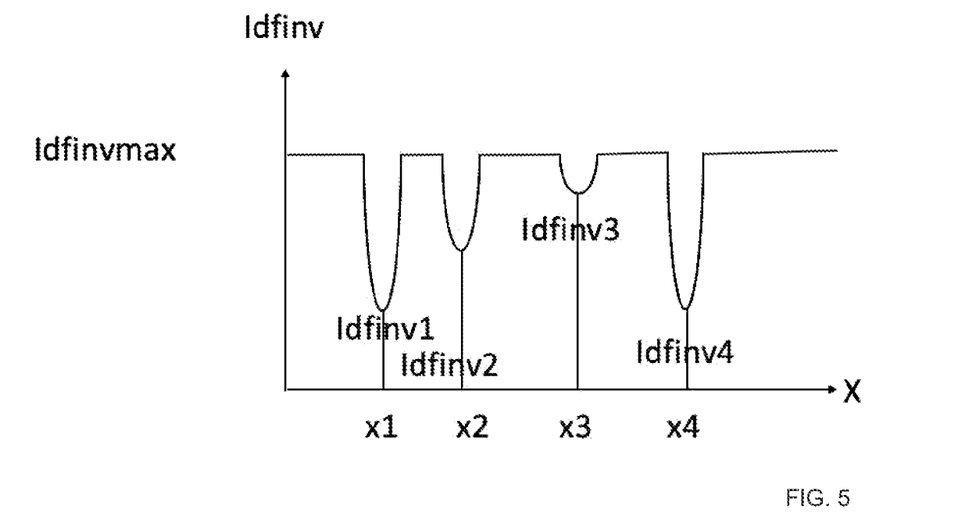
FIG. 5 is a graphical representation of an inverse of FIG. 4.

According to the invention and as shown in FIG. 5, an inverted dark field Idfinv graph is generated by a computer processing unit. The inverted graph Idfinv can, for example, be obtained by a transformation, such as Idfinv (x, y)=Idfmax−Idf (x, y) with, for example Idfmax=255.

Consequently, according to the invention, what may be referred to as a fusion image If is generated by the computer processing unit by adding the image Idfinv and the image Ifc, which can be written If (x, y)=Idfinv (x, y)+Ifc (x, y). Such a fusion image can present the graph represented in FIG. 6.

Figure 6:
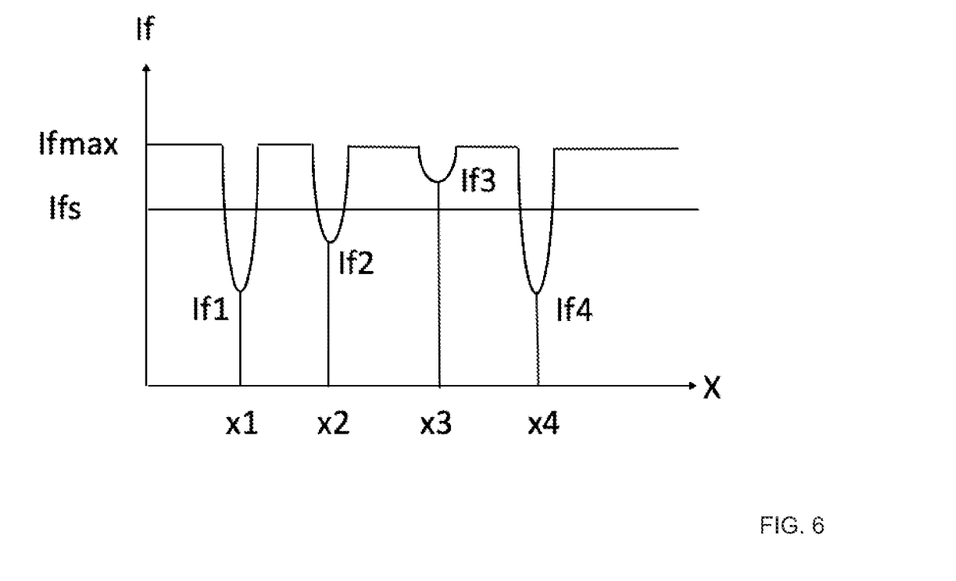
FIG. 6 is a graphical representation of pixel brightness levels of the overlay of the representations of FIG. 2 and FIG. 5.

With the image If thus obtained, one can observe four positions x1, x2, x3, x4 corresponding to the four positions x1 to x4 of the image Ifc and to the four positions x1 to x4 of the image Idf. In the graph of FIG. 6, there is the following relation of order: $If1=If4<If2<If3$.

It is also possible to determine that x1 and x4 are each a marker of the position of a colony. However, such a determination was not the case by only taking into account the image obtained in a bright field. Thus, the linking of the results of the dark field and the bright field helps improve decision making.

Again, the decision could be taken by thresholding by determining a threshold Ifs below which an intensity If is considered indicative of the presence of a colony and above which an intensity If is considered indicative of the absence of a colony.

From the graph of FIG. 6, one can perceive the following relative order: $If1=If4<If2<Ifs<If3$. Based on that, the following decision would be made: a colony is present at x1 and x4 and at x2 and there is an absence of colonies at x3.

As taught herein, the computer processing unit can be configured to count colonies based on a threshold of the fusion image.

In the example which has just been described, the inverted image of that obtained in the dark field configuration was implemented. Within the scope of the invention, the inverted image could have been determined by operation of that obtained in the bright field configuration and added to that obtained in the dark field.

In the example just described, variations in intensity have been shown along a single dimension for reasons of simplicity.

Of course, the variations in intensity level could have been illustrated with a surface rather than a curve. Indeed, the sensors 15 and 25 are matrix sensors forming two-dimensional images.

In the example just described, variations in intensity per pixel were shown. The invention can also be extended to color variations.

More generally, the fusion image can be obtained by combining two operand images, one of the operand images being an inverted image of the image in bright field, respectively in dark field, and the other operand image being the dark field image, respectively bright field. Stated alternatively, one of the operand images may be an inverted image of the bright field image while the other operand image may be the dark field image or one of the operand images may be an inverted image of the dark field image while the other operand image is the bright field image. One can thus write, for example: If (x, y)=C1*Ifc (x, y)+C2*Idfinv (x, y) with C1 and C2 of the same sign, for example between 0 and 1, and where the sum of the two absolute values of C1 and C2 is equal to 1.

Figure 7:
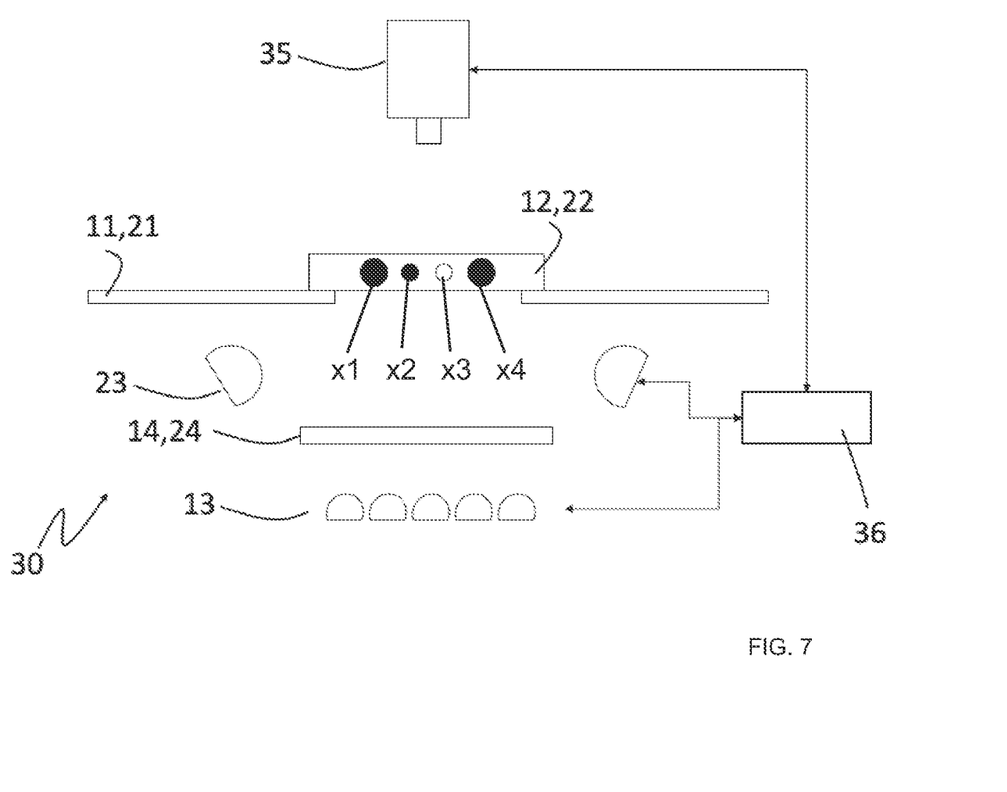
FIG. 7 is a schematic representation of an embodiment of a device according to the invention.

As illustrated by FIG. 7, there is shown an embodiment according to the invention which provides an imaging device 30 for counting colonies present in a sample. As in earlier embodiments, a detection unit 35, such as a matrix photoelectric sensor, is provided. The detection unit 35 may alternatively be referred to as a collection member or unit.

A computer processing unit 36 is designed to selectively control, in a bright field configuration: the replacement of the dark diffusing surface 24 by the light diffusing surface 14; the extinction of light-emitting diodes 23; the lighting of the light-emitting diodes 13; generation of a bright field image from light transmitted by the sample retained in a Petri dish 12, 22 and collected by the detection unit 35. The light-emitting diodes 13 and 23 can be configured and operated as shown and described previously.

The processing unit 36 is designed to selectively control, in a dark field configuration: the replacement of the light diffusing surface 14 by the dark diffusing surface 24; the extinction of light-emitting diodes 13; the lighting of the light-emitting diodes 23; generation of a dark field image from light scattered by the sample retained in the Petri dish 12, 22 and collected by the detection unit 35.

According to one possibility, the light diffusing surface 14 and the dark diffusing surface 24 can be produced by the same surface, in a material allowing switching alternately from one mode to the other. There would then no longer be a need to implement the aforementioned replacement steps. The processing unit 36 is further configured to generate the fusion image and to count the colonies as previously described.

Of course, the different characteristics, shapes, variants and embodiments of the invention can be associated with each other in various combinations as long as they are not incompatible or exclusive of each other. In particular, the variants and embodiments described above could be combined with one another.

It will thus be understood that any terms of orientation referenced herein merely operate to provide a complete understanding of the disclosed invention but do not limit the invention in any respect. Other nomenclature and conventions may be used without limitation of the teachings herein. Furthermore, the various components disclosed herein are merely illustrative and are not limiting of the invention. For example, except as expressly limited by the claims, each of the components discussed herein may include subcomponents that collectively provide for the structure and function of the disclosed component. Furthermore, one or more components, sometimes referred to as members, units, or otherwise herein, could be combined as a unitary structure while still corresponding to the disclosed components. Additional components that provide additional functions, or enhancements to those introduced herein, may be included. For example, additional components and materials, combinations of components or materials, and perhaps the omission of components or materials may be used to create embodiments that are nonetheless within the scope of the teachings herein.

When introducing elements of the present invention or embodiments thereof, the articles "a," "an," and "the" are intended to mean that there are one or more of the elements. The terms "comprising," "including," and "having" are intended to be inclusive such that there may be additional elements other than the listed elements. As used herein, terms such as "example" or "exemplary" are not intended to imply a superlative example. Rather, "exemplary" refers to an embodiment that is one of many possible embodiments.

With certain details and embodiments of the present invention for an image processing device and method disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the following claims shall define the scope of protection to be afforded to the invention. Those claims shall be deemed to include equivalent constructions insofar as they do not depart from the spirit and scope of the invention. It must be further noted that a plurality of the following claims may express, or be interpreted to express, certain elements as means for performing a specific function, at times without the recital of structure or material. As the law demands, any such claims shall be construed to cover not only the corresponding structure and material expressly described in this specification but also all legally-cognizable equivalents thereof.

What is claimed as deserving the protection of Letters Patent:

1. A method of counting colonies present in a sample placed in a support arranged to receive the sample and a solid nutrient medium, the method comprising:
   providing a computer processing unit;
   providing a detection unit in electronic communication with the computer processing unit;
   generating a bright field image from light transmitted through the sample and the medium in a bright field configuration with a light intensity having a maximum value (Ifcmax), wherein the detection unit is positioned to collect the bright field image of positions on the sample, wherein the light intensity exhibits a value (Ifc(x, y)) less than the maximum value indicative of the presence of an occultation in the sample or the medium, and wherein a threshold bright field light intensity (Ifcs) is indicative of a presence of a colony detected by the bright field image;
   generating a dark field image of the positions on the sample from light scattered from the sample and the medium in a dark field configuration, wherein the detection unit is positioned to collect light scattered by the sample and the medium, wherein, in the presence of a colony or opacity deviation in the sample or the medium, the light scattered by the sample and the medium exhibits an increased value (Idf(x, y)) indicative of the presence of the colony or opacity deviation, and wherein a threshold dark field light intensity (Idfs) is indicative of a presence of a colony detected by the dark field image;
   generating a fusion image (If) of the positions on the sample by the computer processing unit, the fusion image (If) obtained by a linear combination of two operand images, wherein one of the operand images is an inverted image of the bright field image and the other operand image is the dark field image or one of the operand images is an inverted image of the dark field image and the other operand image is the bright field image;
   counting colonies of the sample by the computer processing unit based on a processing of the fusion image (If), wherein the processing of the fusion image (If) comprises a thresholding of the fusion image based on a predetermined fusion image threshold light intensity (Ifs) above which a light intensity is considered not to be indicative of a presence of a colony and below which a light intensity is considered to be indicative of a presence of a colony;
   wherein the fusion image (If) obtained by the linear combination of the two operand images is operative to produce an indication of a presence of colonies in positions on the sample and wherein the fusion image threshold light intensity (Ifs) and the computer processing unit are operative to indicate a presence of colonies in positions on the sample including in instances where the presence and location of the colonies would not be indicated by the dark field image or the light field image taken alone.

2. A method of counting colonies present in a sample placed in a support arranged to receive the sample and a solid nutrient medium, the method comprising:
   providing a computer processing unit;
   providing a detection unit in electronic communication with the computer processing unit;
   generating a bright field image from light transmitted through the sample and the medium in a bright field configuration with a light intensity having a maximum value (Ifcmax), wherein the detection unit is positioned to collect the bright field image, wherein the light intensity exhibits a value (Ifc(x, y)) less than the maximum value indicative of the presence of an occultation in the sample or the medium, and wherein a threshold bright field light intensity (Ifcs) is indicative of a presence of a colony detected by the bright field image;

generating a dark field image from light scattered from the sample and the medium in a dark field configuration, wherein the detection unit is positioned to collect light scattered by the sample and the medium, wherein, in the presence of a colony or opacity deviation in the sample or the medium, the light scattered by the sample and the medium exhibits an increased value (Idf(x, y)) indicative of the presence of the colony or opacity deviation, and wherein a threshold dark field light intensity (Idfs) is indicative of a presence of a colony detected by the dark field image;

generating a fusion image (If) by the computer processing unit, the fusion image (If) obtained by a linear combination of two operand images, wherein one of the operand images is an inverted image of the bright field image and the other operand image is the dark field image or one of the operand images is an inverted image of the dark field image and the other operand image is the bright field image;

counting colonies of the sample by the computer processing unit based on a processing of the fusion image (If), wherein the processing of the fusion image (If) comprises a thresholding of the fusion image based on a predetermined fusion image threshold light intensity (Ifs) above which a light intensity is considered not to be indicative of a presence of a colony and below which a light intensity is considered to be indicative of a presence of a colony;

wherein the computer processing unit is operative to generate an inverted dark field graph wherein the light intensity of pixels on the detection unit are graphed in x and y directions as Idf(x,y) and wherein the inverted dark field graph is obtained by the formula Idfinv(x, y)=Idfmax−Idf(x, y).

3. The method of claim 2, wherein the fusion image (If) obtained by the linear combination of the two operand images is performed by the computer processing unit by addition based on the formula If(x, y)=Idfinv(x, y)+Ifc(x, y).

4. The method of claim 3, wherein the fusion image (If) obtained by the linear combination of the two operand images is operative to produce an indication of a presence of colonies in positions on the sample and wherein the fusion image threshold light intensity (Ifs) and the computer processing unit are operative to indicate a presence of colonies in positions on the sample including in instances where the presence and location of the colonies would not be indicated by the dark field image or the light field image taken alone.

5. An image processing device for counting colonies present in a sample, the device provided with a location adapted to receive a support arranged to receive a solid nutrient medium and the sample, wherein the image processing device comprises:

a detection unit operative to generate a bright field image from light transmitted through the sample and the medium in a bright field configuration and collected by the detection unit, wherein the bright field image has a light intensity with a maximum value (Ifcmax), wherein the detection unit is positioned to collect the bright field image of positions on the sample, wherein the light intensity exhibits a value (Ifc(x, y)) less than the maximum value indicative of the presence of an occultation in the sample or the medium, and wherein a threshold bright field light intensity (Ifcs) is indicative of a presence of a colony detected by the bright field image;

the detection unit operative to generate a dark field image of the positions on the sample from light scattered from the sample and the medium in a dark field configuration and collected by the detection unit, wherein the detection unit is positioned to collect light scattered by the sample and the medium, wherein, in the presence of a colony or opacity deviation in the sample or the medium, the light scattered by the sample and the medium exhibits an increased value (Idf(x, y)) indicative of the presence of the colony or opacity deviation, and wherein a threshold dark field light intensity (Idfs) is indicative of a presence of a colony detected by the dark field image;

a computer processing unit operative to generate a fusion image (If) of the positions on the sample, the fusion image (If) obtained by a linear combination of two operand images, wherein one of the operand images is an inverted image of the bright field image and the other operand image is the dark field image or one of the operand images is an inverted image of the dark field image and the other operand image is the bright field image;

wherein the computer processing unit is operative to count colonies of the sample based on a processing of the fusion image (If), wherein the processing of the fusion image (If) comprises a thresholding of the fusion image based on a predetermined fusion image threshold light intensity (Ifs) above which a light intensity is considered not to be indicative of a presence of a colony and below which a light intensity is considered to be indicative of a presence of a colony;

wherein the fusion image (If) obtained by the linear combination of the two operand images is operative to produce an indication of a presence of colonies in positions on the sample and wherein the fusion image threshold light intensity (Ifs) and the computer processing unit are operative to indicate a presence of colonies in positions on the sample including in instances where the presence and location of the colonies would not be indicated by the dark field image or the light field image taken alone.

6. The image processing device of claim 5, further comprising a light diffusing surface and a bright field light source for establishing the bright field configuration and a dark diffusing surface and a dark field light source for establishing the dark field configuration.

7. The image processing device of claim 6, wherein the bright field light source comprises a first plurality of light emitting diodes and wherein the dark field light source comprises a second plurality of light emitting diodes.

8. The image processing device of claim 6, wherein the computer processing unit is selectively operative to establish the bright field configuration wherein the dark field light source is extinguished and the bright field light source is illuminated to illuminate the medium and the sample with light diffused by the light diffusing surface and wherein the computer processing unit is selectively operative to establish the dark field configuration wherein the bright field light source is extinguished and the dark field light source is illuminated to illuminate the medium and the sample with light diffused by the dark diffusing surface.

9. The image processing device of claim 6, wherein the light diffusing surface and the dark diffusing surface are formed by a single diffuser.

10. An image processing device for counting colonies present in a sample, the device provided with a location adapted to receive a support arranged to receive a solid nutrient medium and the sample, wherein the image processing device comprises:
- a detection unit operative to generate a bright field image from light transmitted through the sample and the medium in a bright field configuration and collected by the detection unit, wherein the bright field image has a light intensity with a maximum value (Ifcmax), wherein the detection unit is positioned to collect the bright field image, wherein the light intensity exhibits a value (Ifc(x, y)) less than the maximum value indicative of the presence of an occultation in the sample or the medium, and wherein a threshold bright field light intensity (Ifcs) is indicative of a presence of a colony detected by the bright field image;
- the detection unit operative to generate a dark field image from light scattered from the sample and the medium in a dark field configuration and collected by the detection unit, wherein the detection unit is positioned to collect light scattered by the sample and the medium, wherein, in the presence of a colony or opacity deviation in the sample or the medium, the light scattered by the sample and the medium exhibits an increased value (Idf(x, y)) indicative of the presence of the colony or opacity deviation, and wherein a threshold dark field light intensity (Idfs) is indicative of a presence of a colony detected by the dark field image;
- a computer processing unit operative to generate a fusion image (If), the fusion image (If) obtained by a linear combination of two operand images, wherein one of the operand images is an inverted image of the bright field image and the other operand image is the dark field image or one of the operand images is an inverted image of the dark field image and the other operand image is the bright field image;
- wherein the computer processing unit is operative to count colonies of the sample based on a processing of the fusion image (If), wherein the processing of the fusion image (If) comprises a thresholding of the fusion image based on a predetermined fusion image threshold light intensity (Ifs) above which a light intensity is considered not to be indicative of a presence of a colony and below which a light intensity is considered to be indicative of a presence of a colony;
- wherein the computer processing unit is operative to generate an inverted dark field graph wherein the light intensity of pixels on the detection unit are graphed in x and y directions as Idf(x,y) and wherein the inverted dark field graph is obtained by the formula Idfinv(x, y)=Idfmax−Idf(x, y).

11. The image processing device of claim 10, wherein the fusion image (If) obtained by the linear combination of the two operand images is performed by the computer processing unit by addition based on the formula If(x, y)=Idfinv(x, y)+Ifc(x, y).

12. The image processing device of claim 11, wherein the fusion image (If) obtained by the linear combination of the two operand images is operative to produce an indication of a presence of colonies in positions on the sample and wherein the fusion image threshold light intensity (Ifs) and the computer processing unit are operative to indicate a presence of colonies in positions on the sample including in instances where the presence and location of the colonies would not be indicated by the dark field image or the light field image taken alone.

* * * * *